United States Patent
Ellis et al.

(10) Patent No.: US 8,594,949 B2
(45) Date of Patent: *Nov. 26, 2013

(54) BIOMARKERS FOR DIFFERENTIATING BETWEEN TYPE 1 AND TYPE 2 DIABETES

(75) Inventors: Tamir M. Ellis, Gainesville, FL (US); Alba Esther Morales, Maumelle, AR (US); Mark A. Atkinson, Gainesville, FL (US); Clive H. Wasserfall, Gainesville, FL (US)

(73) Assignee: University of Florida Research Foundation, Inc., Gainesville, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 13/245,287

(22) Filed: Sep. 26, 2011

(65) Prior Publication Data

US 2012/0077709 A1 Mar. 29, 2012

Related U.S. Application Data

(60) Continuation of application No. 12/689,102, filed on Jan. 18, 2010, now abandoned, and a division of application No. 10/873,101, filed on Jun. 21, 2004, now Pat. No. 7,648,825.

(60) Provisional application No. 60/480,041, filed on Jun. 20, 2003.

(51) Int. Cl.
*G01N 33/48* (2006.01)
*G01N 31/00* (2006.01)
*G06G 7/48* (2006.01)
*G06G 7/58* (2006.01)

(52) U.S. Cl.
USPC ............ 702/19; 702/22; 703/11; 703/12

(58) Field of Classification Search
None
See application file for complete search history.

(56) References Cited

U.S. PATENT DOCUMENTS

| | | | |
|---|---|---|---|
| 6,448,086 B1 | 9/2002 | Khosravi et al. | |
| 7,067,634 B2 | 6/2006 | Tomita et al. | |
| 2003/0013120 A1* | 1/2003 | Patz et al. | 435/7.1 |
| 2003/0048565 A1 | 3/2003 | Tamura | |
| 2004/0153249 A1 | 8/2004 | Zhang et al. | |
| 2005/0048565 A1* | 3/2005 | Tomita et al. | 435/7.1 |

FOREIGN PATENT DOCUMENTS

| | | |
|---|---|---|
| EP | 04821560.2 | 10/2008 |
| WO | WO 98/11435 | 3/1998 |
| WO | WO 03/016906 | 2/2003 |

OTHER PUBLICATIONS

Imagawa et al. (Diabetes Care, 2002, 25(9), 1665-1666).*
Rodriguez-Villar et al. (Diabetes Research and Clinical Practice, 1997, 37, 145-148).*
Hanaki et al., (Journal of Clinical Endocrinology & Metabolism, 1999, 84(5), 1524-1526).*
Chen et al. (Exp. Anim., vol. 52, No. 2, p. 137-143, Apr. 2003).*

(Continued)

*Primary Examiner* — Larry D Riggs, II
(74) *Attorney, Agent, or Firm* — Saliwanchik, Lloyd & Eisenschenk

(57) ABSTRACT

Biomarkers that are diagnostic of type 1 diabetes, type 2 diabetes and/or diabetic disorder are identified. Detection of different biomarkers of the invention are also diagnostic of the degree of severity of type 1 diabetes, type 2 diabetes and/or diabetic disorder. An analysis includes the parameters of matching for BMI and Tanner stage. Receiver-operator characteristic (ROC) curves were established to assess association of the biomarkers with a disease.

13 Claims, 5 Drawing Sheets

(56) References Cited

OTHER PUBLICATIONS

Hotta et al. (Arterioscler. Thromb. Vasc. Biol., vol. 20, p. 1595-1599, 2000).*
Havel (Current Opinion in Lipidology, vol. 13, p. 51-91, 2002).*
Yamauchi et al. (Nature Medicine, vol. 7, No. 8, p. 941-946, Aug. 2001).*
Chen et al. Ratio of leptin to adiponectin as an obesity index of cynomolgus monkeys (mascara fascicularis), *Exp. Anim.*, Apr. 2003, pp. 137-143, vol. 52, No. 2.
Fehmann et al. "Plasma Resistin Levels in Patients with Type 1 and Type 2 Diabetes Mellitus and in Healthy Controls" *Horm Metab Res*, 2002, pp. 671-673, vol. 34.
Hanaki et al. "Leptin before and after insulin therapy in children with new-onset type 1 diabetes" *Journal of clinical Endocrinology and Metabolism*, 1999, pp. 1524-1526, vol. 84, No. 5.
Havel "Control of energy homeostasis and insulin action by adipocyte hormones: leptin, acylation stimulating protein, and adiponectin" *Current Opinion in Lipidology*, 2002, p. 51-91, vol. 13.
Hotta et al. "Plasma concentrations of a novel, adipose-specific protein, adiponectin, in type 2 diabetic patients" *Arterioscler. Thromb. Vase. Biol.*, 2000, pp. 1595-1599, vol. 20.
Imagawa, A. et 31.: Elevated Serum Concentration of Adipose-*Derived* Factor, Adiponectin, in Patients with Type 1 Diabetes. Diabetes Care. 2002, vol. 25, pp. 1665-1666.
Kiess et al. "Serum leptin levels in children and adolescents with insulin-dependent diabetes mellitus in relation to metabolic control and body mass index" *European Journal of Endocrinology*, 1998, pp. 501-509, vol. 138.
McNeely et al. "Association Between Baseline Plasma Leptin Levels and Subsequent Development of Diabetes in Japanese Americans" *Diabetes Care*, 1999, vol. 22, pp. 65-70.
Mishima et al. "Relationship Between Serum Tumor Necrosis Factor-$\alpha$ and Insulin Resistance in Obese Men with Type 2 Diabetes Mellitus" *Diabetes Research and Clinical Practice*, 2001, pp. 119-123, vol. 52.
Pihoker et al. "Autoantibodies in Diabetes" *Diabetes*, 2005, pp. S52-S61, vol. 54, Suppl. 2.
Pradhan et al. "C-Reactive Protein, Interleukin 6, and Risk of Developing Type 2 Diabetes Mellitus" *JAMA*, 2001, pp. 327-334, vol. 286.
Quintana et al. "Cluster Analysis of Human Autoantibody Reactivities in Health and in Type 1 Diabetes Mellitus: A Bio-Informatic Approach to Immune Complexity" *Journal of Autoimmunity*, 2003, pp. 65-75, vol. 21.
Rodriguez-Villar, C. "High proinsulin levels in late PRE-IDDM stage" *Diabetes Research and Clinical Practices*, 1997, pp. 145-148, vol. 37.
Ruhl C.E. et al: "Leptin concentrations in the United States: Relations with demographic and anthropometric measures" *American Journal of Clinical Nutrition*, 2001, pp. 295-301, vol. 74.
Satoh et al. "Leptin-to-adiponectin ration as a potential atherogenic index in obese type 2 diabetic patients" *Diabetes Care*, Oct. 2004, pp. 2488-2490, vol. 27, No. 10.
Setoguchi et al. "Homeostatic Maintenance of Natural $Foxp3^+$ $CD25^+$ $CD4^+$ Regulatory T Cells by Interleukin (IL)-2 and Induction of Autoimmune Disease by IL-2 Neutralization" *JEM*, 2005, pp. 723-735, vol. 201, No. 5.
Shiiya et al. "Plasma Ghrelin Levels in Lean and Obese Humans and the Effect of Glucose on Ghrelin Secretion," *Journal of Clinical Endocrinology & Metabolism*, 2002, pp. 240-244, vol. 87, No. 1.
Shuldiner, Alan R. et al.: Resistin, Obesity and Insulin Resistance-the Emerging Role of the Adipocyte as an Endocrine Organ. New England Journal of Medicine. 2001, vol. 345, No. 18,pp. 1345-1346.
Spranger J. et al: "Adiponectin and protection against type 2 diabetes mellitus" *The Lancet*, 2003, pp. 226-228, vol. 361.
Stefan N. et al.: "Adiponectin—Its role in metabolism and beyond" *Horm Metab Res.*, 2002, pp. 469-474, vol. 34.
Vilsboll et al. "Incretin Secretion in Relation to Meal Size and Body Weight in Healthy Subjects and People with Type 1 and Type 2 Diabetes Mellitus" *J. Clin. Endocrinol. Metab.*, 2003, pp. 2706-2713, vol. 88.
Werle, E. et al, "Apolipoprotein E Polymorphism and Renal Function in German Type 1 and Type 2 Diabetic Patients"; *Diabetes Care*; Jun. 1998; p. 994-998.
Yamada, K. et al. "Combined measurements of GAD65 and ICA512 antibodies in acute onset and slowly progressive IDDM" *Diabetes Research and Clinical Practice*, 1997, pp. 91-98, vol. 35, No. 2-3.
Yamauchi et al. "The fat-derived hormone adiponectin reverses insulin resistance associated with both lipoatrophy and obesity" *Nature Medicine*, 2001, pp. 941-946, vol. 7, No. 8.

\* cited by examiner

BIOMARKERS FOR DIFFERENTIATING BETWEEN TYPE 1 AND TYPE 2 DIABETES

This application is a continuation application of U.S. application Ser. No. 12/689,102, filed Jan. 18, 2010, now abandoned; which is a divisional application of U.S. application Ser. No. 10/873,101, filed Jun. 21, 2004, now U.S. Pat. No. 7,648,825; which claims the benefit of U.S. Provisional Application No. 60/480,041, filed Jun. 20, 2003; which are hereby incorporated by reference in their entirety.

FIELD OF THE INVENTION

The invention provides for the reliable detection and identification of biomarkers, important for the diagnosis and prognosis of type 1 diabetes, type 2 diabetes and/or diabetic disorders. More particularly, the invention relates to compositions and methods for differentiating between type 1 and type 2 diabetes by measuring levels of adiponectin and leptin.

BACKGROUND

A worldwide epidemic exists with respect to diabetes; a fact in large part due to increased rates of obesity. Recent studies have established adipose tissue as an endocrine organ capable of hormone and cytokine secretion. Adiponectin, is an anti-inflammatory and anti-atherogenic hormone exclusively synthesized in adipose tissue. Serum adiponectin levels are decreased in obese adults including those with Type 2 diabetes (T2D), and increase during weight loss or treatment with thiazolidinediones. Indeed, adiponectin has been proposed to independently protect against T2D. Adiponection appears to increase insulin sensitivity by regulating glucose and lipid metabolism. Indeed, a major effect of adiponectin involves the enhancement of insulin action in liver and hence, hepatic glucose output.

Leptin, another obesity related hormone, is critical in the regulation of energy balance and body weigh. Like adiponectin, it also is secreted mainly by adipocytes. However, in contrast to adiponectin, leptin concentration in serum is decreased in obese adults including those with T2D. Leptin levels are directly correlated with total body fat.

Detection and diagnosis of diabetes has proved to be difficult to asses in children and adolescents. There is therefore, an urgent need in the art to identify markers that discriminate between type 1 and type 2 diabetes and/or metabolic disorders.

SUMMARY

The present invention identifies protein markers that are differentially present in the samples of patients suffering from type 1 diabetes, type 2 diabetes and/or diabetic disorders as compared to samples of control subjects. The present invention also provides sensitive and quick methods and kits that can be used as an aid for diagnosis of type 1 diabetes, type 2 diabetes and/or diabetic disorders by detecting these markers. The measurement of these markers, alone or in combination, in patient samples provides information that a diagnostician can correlate with a probable diagnosis of the extent of type 1 diabetes, type 2 diabetes and/or diabetic disorder.

In a preferred embodiment, the invention provides a method for differentiating between type 1 and type 2 diabetes in a pediatric subject. Preferably, the method comprises the steps of obtaining a serum sample from the subject; determining the amount of biomarker in the sample; and correlating the amount of at least one biomarker in the sample with the presence of either type 1 and type 2 diabetes in the subject.

In another preferred embodiment, the levels of at least two biomarkers in the sample are determined and extrapolated into a ratio and the ratio is correlated with the presence of either type 1 and type 2 diabetes in the subject. Preferably, the ratio is calculated by a multivariant analysis associating biomarker levels with anthropometrical parameters and disease state.

In another preferred embodiment, the multivariant analysis further includes matching for BMI and Tanner stage. Preferably, the ratio of biomarkers is determined by differences in receiver-operator characteristic (ROC) curves. In accordance with the invention, the calculation of area under the receiver-operator characteristic (ROC) curves determines the ratio of biomarkers.

In another preferred embodiment, calculation of the ratio of biomarkers is determines specificity for type 1 or type 2 diabetes. Preferably, specific detection of biomarker ratios is about 70% as compared to a healthy subject, more preferable, specific detection of biomarker ratios is about 90% as compared to a healthy subject, more preferable, specific detection of biomarker ratios is up to 100% as compared to a healthy subject.

In another preferred embodiment, calculation of the ratio of biomarkers is determines sensitivity for type 1 or type 2 diabetes biomarkers. Preferably, the sensitivity of detection of biomarker ratios is about 70% as compared to a healthy subject, more preferable, sensitivity of detection of biomarker ratios is about 90% as compared to a healthy subject, more preferable, sensitivity of detection of biomarker ratios is up to 100% as compared to a healthy subject.

In another preferred embodiment, the ratio of at least two biomarkers differentiates between type 1 and type 2 diabetes in a subject.

In a preferred embodiment, the invention provides a method for differentiating between type 1 and type 2 diabetes in a pediatric subject. Preferably, the method comprises the steps of obtaining a serum sample from the subject; determining the amount of adiponectin or leptin in the sample; and correlating the amount of adiponectin or leptin in the sample with the presence of either type 1 and type 2 diabetes in the subject. Preferably, other biomarkers include, but not limited to, for example, ghrelin, resistin, autoantibodies to insulin, autoantibodies to glutamic acid decarboxylase, autoantibodies to IL-2, autoantibodies to IA-2, incretins, TNF-α, and IL-6.

In another preferred embodiment, the levels of both adiponectin and leptin in the sample are determined and extrapolated into a ratio (adiponectin:leptin or leptin:adiponectin), or any combination thereof, including, but not limited to ghrelin, resistin, autoantibodies to insulin, autoantibodies to glutamic acid decarboxylase, autoantibodies to IL-2, autoantibodies to IA-2, incretins, TNF-α, and IL-6, and the ratio is correlated with the presence of either type 1 and type 2 diabetes in the subject.

In another preferred embodiment, the ratio is calculated by a multivariant analysis associating serum adiponectin and leptin levels with anthropometrical parameters and disease state. Preferably, the multivariant analysis further includes matching for BMI and Tanner stage.

In another preferred embodiment, the ratio of adiponectin and leptin biomarkers is determined by differences in receiver-operator characteristic (ROC) curves. In accordance with the invention, calculation of area under the receiver-operator characteristic (ROC) curves determines the ratio of adiponectin and lectin biomarkers.

In another preferred embodiment, calculation of the ratio of adiponectin and leptin determines specificity for type 1 or type 2 diabetes. Preferably, wherein specific detection of adiponectin and lectin biomarker ratios is about 70% as compared to a healthy subject, more preferable, specific detection of adiponectin and lectin biomarker ratios is about 90% as compared to a healthy subject, more preferable, specific detection of adiponectin and lectin biomarker ratios is up to 100% as compared to a healthy subject.

In another preferred embodiment, calculation of the ratio of adiponectin and leptin determines sensitivity for type 1 or type 2 diabetes. Preferably, sensitivity of detection of adiponectin and lectin biomarker ratios is about 70% as compared to a healthy subject, more preferable, sensitivity of detection of adiponectin and lectin biomarker ratios is about 90% as compared to a healthy subject, more preferable, sensitivity of detection of adiponectin and lectin biomarker ratios is up to 100% as compared to a healthy subject.

In another aspect, preferably a single biomarker is used in combination with one or more biomarkers from normal, healthy individuals for diagnosing type 1 diabetes, type 2 diabetes and/or diabetic disorder and progression of disease, more preferably a plurality of the markers are used in combination with one or more biomarkers from normal, healthy individuals for diagnosing type 1 diabetes, type 2 diabetes and/or diabetic disorder and progression of disease. It is preferred that one or more protein biomarkers are used in comparing protein profiles from patients susceptible to, or suffering from type 1 diabetes, type 2 diabetes and/or diabetic disorder diagnosis, with normal subjects. For example, adiponectin, leptin, ghrelin, resistin, autoantibodies to insulin, autoantibodies to glutamic acid decarboxylase, autoantibodies to IL-2, autoantibodies to IA-2, incretins, TNF-α, and IL-6, fragments, variants or any combination thereof.

In another preferred embodiment, detection methods include use of a biochip array. Biochip arrays useful in the invention include protein and nucleic acid arrays. One or more markers are immobilized on the biochip array and subjected to laser ionization to detect the molecular weight of the markers. Analysis of the markers is, for example, by molecular weight of the one or more markers against a threshold intensity that is normalized against total ion current. Preferably, logarithmic transformation is used for reducing peak intensity ranges to limit the number of markers detected.

In another preferred method, data is generated on immobilized subject samples on a biochip array, by subjecting said biochip array to laser ionization and detecting intensity of signal for mass/charge ratio; and, transforming the data into computer readable form; and executing an algorithm that classifies the data according to user input parameters, for detecting signals that represent markers present in type 1 diabetes, type 2 diabetes and/or diabetic disorder patients and are lacking in non-diabetic and/or non-diseased subject controls.

Preferably the biochip surfaces are, for example, ionic, anionic, comprising immobilized nickel ions, a mixture of positive and negative ions, one or more antibodies, single or double stranded nucleic acids, proteins, peptides or fragments thereof, amino acid probes, phage display libraries.

In other preferred methods one or more of the markers are detected using laser desorption/ionization mass spectrometry, comprising, providing a probe adapted for use with a mass spectrometer comprising an adsorbent attached thereto, and; contacting the subject sample with the adsorbent, and; desorbing and ionizing the marker or markers from the probe and detecting the deionized/ionized markers with the mass spectrometer.

Preferably, the laser desorption/ionization mass spectrometry comprises, providing a substrate comprising an adsorbent attached thereto; contacting the subject sample with the adsorbent; placing the substrate on a probe adapted for use with a mass spectrometer comprising an adsorbent attached thereto; and, desorbing and ionizing the marker or markers from the probe and detecting the desorbed/ionized marker or markers with the mass spectrometer.

The adsorbent can for example be, hydrophobic, hydrophilic, ionic or metal chelate adsorbent, such as, nickel or an antibody, single- or double stranded oligonucleotide, amino acid, protein, peptide or fragments thereof.

In another embodiment, a process for purification of a biomarker, comprising fractioning a sample comprising one or more protein biomarkers by size-exclusion chromatography and collecting a fraction that includes the one or more biomarker; and/or fractionating a sample comprising the one or more biomarkers by anion exchange chromatography and collecting a fraction that includes the one or more biomarkers. Fractionation is monitored for purity on normal phase and immobilized nickel arrays. Generating data on immobilized marker fractions on an array, is accomplished by subjecting said array to laser ionization and detecting intensity of signal for mass/charge ratio; and, transforming the data into computer readable form; and executing an algorithm that classifies the data according to user input parameters, for detecting signals that represent markers present in type 1 diabetes, type 2 diabetes and/or diabetic disorder patients and are lacking in non-diabetic and/or non-diseased subject controls. Preferably fractions are subjected to gel electrophoresis and correlated with data generated by mass spectrometry. In one aspect, gel bands representative of potential markers are excised and subjected to enzymatic treatment and are applied to biochip arrays for peptide mapping.

In another preferred embodiment, the presence of certain biomarkers is indicative of the extent of type 1 diabetes, type 2 diabetes and/or diabetic disorder. For example, detection of one or more biomarkers would be indicative of type 1 diabetes, type 2 diabetes and/or diabetic disorder and the presence of one or more would be indicative of the extent of type 1 diabetes, type 2 diabetes and/or diabetic disorder diagnosis. Preferably, the biomarkers can be compared to a known protein indicative of diabetes such as the insulin levels.

Preferred methods for detection and diagnosis of type 1 diabetes, type 2 diabetes and/or diabetic disorder comprise detecting at least one or more protein biomarkers in a subject sample, and; correlating the detection of one or more protein biomarkers with a diagnosis of type 1 diabetes, type 2 diabetes and/or diabetic disorder, wherein the correlation takes into account the detection of one or more biomarker in each diagnosis, as compared to normal subjects, wherein the one or more protein markers comprise, for example, adiponectin, lectin and insulin.

In another preferred embodiment, the invention provides a kit for analyzing type 1 diabetes, type 2 diabetes and/or diabetic disorder in a subject. The kit, preferably includes: (a) a substrate for holding a biological sample isolated from a human subject suspected of having type 1 diabetes, type 2 diabetes and/or diabetic disorder, (b) an agent that specifically binds at least one or more of the diabetic proteins; and (c) printed instructions for reacting the agent with the biological sample or a portion of the biological sample to detect the presence or amount of at least one marker in the biological sample.

Preferably, the biological sample is a fluid, for example, blood or serum, and the agent can be an antibody, aptamer, or other molecule that specifically binds at least one or more of the diabetic proteins. The kit can also include a detectable label such as one conjugated to the agent, or one conjugated to a substance that specifically binds to the agent (e.g., a secondary antibody).

Other aspects of the invention are described infra.

DETAILED DESCRIPTION

Figure 1A:
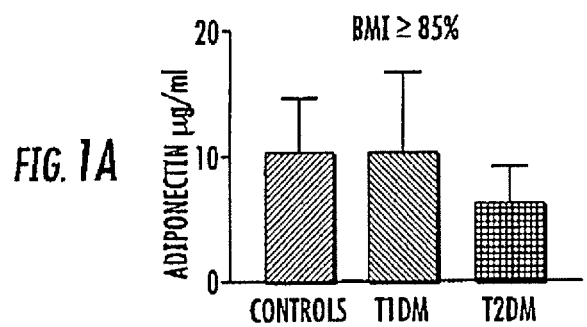
FIG. 1 is a series of graphs showing adiponectin levels (A), leptin (levels), and adiponectin/leptin ratios in the serum of control (non-diabetic), T1D, and T2D pediatric subjects.

The invention provides the research leading to the present invention investigated children and adolescents with diabetes for production of these hormones not only for additional mechanistic information that could be derived but in addition, to identify any diagnostic value these markers would provide in discriminating between these disorders which are sometimes difficult to distinguish in this age group.

Definitions

Prior to setting forth the invention, it may be helpful to an understanding thereof to set forth definitions of certain terms that will be used hereinafter.

"Marker" in the context of the present invention refers to a polypeptide (of a particular apparent molecular weight) which is differentially present in a sample taken from patients having diabetic disorders as compared to a comparable sample taken from control subjects (e.g., a person with a negative diagnosis, normal or healthy subject).

"Complementary" in the context of the present invention refers to detection of at least two biomarkers, which when detected together provides increased sensitivity and specificity as compared to detection of one biomarker alone.

The phrase "differentially present" refers to differences in the quantity and/or the frequency of a marker present in a sample taken from patients having for example, diabetes as compared to a control subject. For example, a marker can be a polypeptide which is present at an elevated level or at a decreased level in samples of patients with diabetes compared to samples of control subjects. Alternatively, a marker can be a polypeptide which is detected at a higher frequency or at a lower frequency in samples of patients compared to samples of control subjects. A marker can be differentially present in terms of quantity, frequency or both.

A polypeptide is differentially present between the two samples if the amount of the polypeptide in one sample is statistically significantly different from the amount of the polypeptide in the other sample. For example, a polypeptide is differentially present between the two samples if it is present at least about 120%, at least about 130%, at least about 150%, at least about 180%, at least about 200%, at least about 300%, at least about 500%, at least about 700%, at least about 900%, or at least about 1000% greater than it is present in the other sample, or if it is detectable in one sample and not detectable in the other.

Alternatively or additionally, a polypeptide is differentially present between the two sets of samples if the frequency of detecting the polypeptide in samples of patients' suffering from diabetic disorders, is statistically significantly higher or lower than in the control samples. For example, a polypeptide is differentially present between the two sets of samples if it is detected at least about 120%, at least about 130%, at least about 150%, at least about 180%, at least about 200%, at least about 300%, at least about 500%, at least about 700%, at least about 900%, or at least about 1000% more frequently or less frequently observed in one set of samples than the other set of samples.

"Diagnostic" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

A "test amount" of a marker refers to an amount of a marker present in a sample being tested. A test amount can be either in absolute amount (e.g., μg/ml) or a relative amount (e.g., relative intensity of signals).

A "diagnostic amount" of a marker refers to an amount of a marker in a subject's sample that is consistent with a diagnosis of Type 1 or Type 2 diabetes and/or diabetic disorders. A diagnostic amount can be either in absolute amount (e.g., μg/ml) or a relative amount (e.g., relative intensity of signals).

A "control amount" of a marker can be any amount or a range of amount which is to be compared against a test amount of a marker. For example, a control amount of a marker can be the amount of a marker in a person without diabetes. A control amount can be either in absolute amount (e.g., μg/ml) or a relative amount (e.g., relative intensity of signals).

As used herein, "diabetic proteins" refers to any protein that is detectable in an individual with type 1 or type 2 diabetes, such as for example, adiponectin, leptin, insulin, ghrelin, resistin, autoantibodies to insulin, autoantibodies to glutamic acid decarboxylase, autoantibodies to IL-2, autoantibodies to IA-2, incretins, TNF-α, and IL-6, fragments, variants or any combination thereof and the like.

As used herein, a "pharmaceutically acceptable" component is one that is suitable for use with humans and/or animals without undue adverse side effects (such as toxicity, irritation, and allergic response) commensurate with a reasonable benefit/risk ratio.

The terms "patient" or "individual" are used interchangeably herein, and is meant a mammalian subject to be treated, with human patients being preferred. In some cases, the methods of the invention find use in experimental animals, in veterinary application, and in the development of animal models for disease, including, but not limited to, rodents including mice, rats, and hamsters; and primates.

As used herein, "ameliorated" or "treatment" refers to a symptom which is approaches a normalized value, e.g., is less than 50% different from a normalized value, preferably is less than about 25% different from a normalized value, more preferably, is less than 10% different from a normalized value, and still more preferably, is not significantly different from a normalized value as determined using routine statistical tests.

"Probe" refers to a device that is removably insertable into a gas phase ion spectrometer and comprises a substrate having a surface for presenting a marker for detection. A probe can comprise a single substrate or a plurality of substrates.

"Substrate" or "probe substrate" refers to a solid phase onto which an adsorbent can be provided (e.g., by attachment, deposition, etc.).

"Adsorbent" refers to any material capable of adsorbing a marker. The term "adsorbent" is used herein to refer both to a single material ("monoplex adsorbent") (e.g., a compound or functional group) to which the marker is exposed, and to a plurality of different materials ("multiplex adsorbent") to which the marker is exposed. The adsorbent materials in a multiplex adsorbent are referred to as "adsorbent species." For example, an addressable location on a probe substrate can comprise a multiplex adsorbent characterized by many different adsorbent species (e.g., anion exchange materials, metal chelators, or antibodies), having different binding characteristics. Substrate material itself can also contribute to adsorbing a marker and may be considered part of an "adsorbent."

"Adsorption" or "retention" refers to the detectable binding between an absorbent and a marker either before or after washing with an eluant (selectivity threshold modifier) or a washing solution.

"Eluant" or "washing solution" refers to an agent that can be used to mediate adsorption of a marker to an adsorbent. Eluants and washing solutions are also referred to as "selectivity threshold modifiers." Eluants and washing solutions can be used to wash and remove unbound materials from the probe substrate surface.

"Resolve," "resolution," or "resolution of marker" refers to the detection of at least one marker in a sample. Resolution includes the detection of a plurality of markers in a sample by separation and subsequent differential detection. Resolution does not require the complete separation of one or more markers from all other biomolecules in a mixture. Rather, any separation that allows the distinction between at least one marker and other biomolecules suffices.

"Gas phase ion spectrometer" refers to an apparatus that measures a parameter which can be translated into mass-to-charge ratios of ions formed when a sample is volatilized and ionized. Generally ions of interest bear a single charge, and mass-to-charge ratios are often simply referred to as mass. Gas phase ion spectrometers include, for example, mass spectrometers, ion mobility spectrometers, and total ion current measuring devices.

"Mass spectrometer" refers to a gas phase ion spectrometer that includes an inlet system, an ionization source, an ion optic assembly, a mass analyzer, and a detector.

"Laser desorption mass spectrometer" refers to a mass spectrometer which uses laser as means to desorb, volatilize, and ionize an analyte.

"Detect" refers to identifying the presence, absence or amount of the object to be detected.

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins.

"Detectable moiety" or a "label" refers to a composition detectable by spectroscopic, photochemical, biochemical, immunochemical, or chemical means. For example, useful labels include $^{32}P$, $^{35}S$, fluorescent dyes, electron-dense reagents, enzymes (e.g., as commonly used in an ELISA), biotin-streptavidin, dioxigenin, haptens and proteins for which antisera or monoclonal antibodies are available, or nucleic acid molecules with a sequence complementary to a target. The detectable moiety often generates a measurable signal, such as a radioactive, chromogenic, or fluorescent signal, that can be used to quantify the amount of bound detectable moiety in a sample. Quantitation of the signal is achieved by, e.g., scintillation counting, densitometry, or flow cytometry.

"Antibody" refers to a polypeptide ligand substantially encoded by an immunoglobulin gene or immunoglobulin genes, or fragments thereof, which specifically binds and recognizes an epitope (e.g., an antigen). The recognized immunoglobulin genes include the kappa and lambda light chain constant region genes, the alpha ($\alpha$), gamma ($\gamma$), delta ($\delta$), epsilon ($\epsilon$), and mu ($\mu$) heavy chain constant region genes, and the myriad immunoglobulin variable region genes. Antibodies exist, e.g., as intact immunoglobulins or as a number of well characterized fragments produced by digestion with various peptidases. This includes, e.g., Fab' and F(ab)'$_2$ fragments. The term "antibody," as used herein, also includes antibody fragments either produced by the modification of whole antibodies or those synthesized de novo using recombinant DNA methodologies. It also includes polyclonal antibodies, monoclonal antibodies, chimeric antibodies, humanized antibodies, or single chain antibodies. "Fc" portion of an antibody refers to that portion of an immunoglobulin heavy chain that comprises one or more heavy chain constant region domains, $CH_1$, $CH_2$ and $CH_3$, but does not include the heavy chain variable region.

"Immunoassay" is an assay that uses an antibody to specifically bind an antigen (e.g., a marker). The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to marker "X" from specific species such as rat, mouse, or human can be selected to obtain only those polyclonal antibodies that are specifically immunoreactive with marker "X" and not with other proteins, except for polymorphic variants and alleles of marker "X". This selection may be achieved by subtracting out antibodies that cross-react with marker "X" molecules from other species. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background.

"Energy absorbing molecule" or "EAM" refers to a molecule that absorbs energy from an ionization source in a mass spectrometer thereby aiding desorption of analyte, such as a marker, from a probe surface. Depending on the size and nature of the analyte, the energy absorbing molecule can be optionally used. Energy absorbing molecules used in MALDI are frequently referred to as "matrix." Cinnamic acid derivatives, sinapinic acid ("SPA"), cyano hydroxy cinnamic acid ("CHCA") and dihydroxybenzoic acid are frequently used as energy absorbing molecules in laser desorption of bioorganic molecules.

"Sample" is used herein in its broadest sense. A sample comprising polynucleotides, polypeptides, peptides, antibodies and the like may comprise a bodily fluid; a soluble fraction of a cell preparation, or media in which cells were grown; a chromosome, an organelle, or membrane isolated or extracted from a cell; genomic DNA, RNA, or cDNA, polypeptides, or peptides in solution or bound to a substrate; a cell; a tissue; a tissue print; a fingerprint, skin or hair; and the like.

"Substantially purified" refers to nucleic acid molecules or proteins that are removed from their natural environment and are isolated or separated, and are at least about 60% free, preferably about 75% free, and most preferably about 90% free, from other components with which they are naturally associated.

"Substrate" refers to any rigid or semi-rigid support to which nucleic acid molecules or proteins are bound and includes membranes, filters, chips, slides, wafers, fibers, magnetic or nonmagnetic heads, gels, capillaries or other tubing, plates, polymers, and microparticles with a variety of surface forms including wells, trenches, pins, channels and pores.

As used herein, "diabetic disorders" refers to complications due to diabetes. For example, complications such as retinopathy, nephropathy and neuropathy develop with angiopathy as a prime factor in diabetic individuals.

As used herein "diabetes" refers to type I and type II diabetes. Diabetes is classified according to the types of disease into insulin dependent diabetes (IDDM; type I diabetes) and non-insulin dependent diabetes (NIDDM; type II diabetes).

In a preferred embodiment, detection of one or more biomarkers is diagnostic for Type 1 and Type 2 diabetes and/or diabetic disorders. For example, detection of adiponectin and/or lectin, ghrelin, resistin, autoantibodies to insulin, autoantibodies to glutamic acid decarboxylase, autoantibodies to IL-2, autoantibodies to IA-2, incretins, TNF-$\alpha$, and IL-6, fragments, peptides or variants thereof. In accordance with the invention, adjusting for BMI and pubertal stage, adiponectin levels were elevated in T1D and decreased in T2D. Conversely, elevations in leptin concentrations were observed in cases of pediatric T2D.

In another preferred embodiment, detection of a biomarkers that are differentially present in an individual are diagnostic of type 1 diabetes, type 2 diabetes and/or diabetic disorders. For example, adiponectin/leptin ratios were dramatically different amongst healthy children (11.8 [95% CI 4.8-18.7]) and those with T1D (6.1 [3.8-8.3] or T2D (0.4 [0.3-0.5]) ($p<0.0001$). Other combinations can include, for example, adiponectin, leptin, ghrelin, resistin, autoantibodies to insulin, autoantibodies to glutamic acid decarboxylase, autoantibodies to IL-2, autoantibodies to IA-2, incretins, TNF-$\alpha$, and IL-6, fragments, variants or any combination thereof.

In another preferred embodiment, the invention provides for the quantitative detection of biomarkers diagnostic of type 1 and type 2 diabetes and/or diabetic disorders. Depending on the type and severity of disease biomarkers are differentially present and the ratios of these biomarkers are indicative of diabetes and/or diabetic disorders. For example, the ratio of adiponectin to leptin as compared to healthy individuals.

In another preferred embodiment, detection of certain biomarkers are diagnostic of the specific type of diabetes. For example, detection of adiponectin and leptin proteins, peptides, fragments and derivatives thereof is diagnostic of type 1 or type 2 diabetes.

In another preferred embodiment, type 1, type 2 and/or diabetic disorders in a subject is analyzed by (a) providing a biological sample isolated from a subject suspected of having diabetes; (b) detecting in the sample the presence or amount of at least one marker selected from one or more biomarker proteins; and (c) correlating the presence or amount of the marker with the presence or type of diabetes in the subject. Preferably, a sample from a diabetic individual, such as serum, adipocytes, pancreatic cells and the like, in in vitro culture or in situ in an animal subjects express higher levels of diabetic proteins as compared to non-diabetic individuals. Preferably, the samples comprise cells, for example, a biopsy of adipocyte tissue and pancreas are suitable biological samples for use in the invention. In addition, adiponectin/lectin are detected in the circulating blood and other biofluids (e.g. urine, sweat, s saliva, etc.). Thus, other suitable biological samples include, but not limited to such cells or fluid secreted from these cells. Obtaining biological fluids such as blood, plasma, serum, saliva and urine, from a subject is typically much less invasive and traumatizing than obtaining a solid tissue biopsy sample. Thus, samples, which are biological fluids, are preferred for use in the invention.

A biological sample can be obtained from a subject by conventional techniques. Blood can be obtained by venipuncture, while plasma and serum can be obtained by fractionating whole blood according to known methods. Surgical techniques for obtaining solid tissue samples are well known in the art.

Any animal that expresses the diabetic biomarker proteins, such as for example, adiponectin, leptin, can be used as a subject from which a biological sample is obtained. Preferably, the subject is a mammal, such as for example, a human, dog, cat, horse, cow, pig, sheep, goat, chicken, primate, rat, or mouse. More preferably, the subject is a human. Particularly preferred are subjects suspected of having or at risk for developing type 1 type 2 diabetes and related diabetic disorders.

In a preferred embodiment, samples are obtained from children and adolescents with type 1 diabetes (n=41), type 2 diabetes (n=17), and nondiabetic individuals of similar age from the general population (n=43) were investigated. An analysis included the parameters of matching for BMI and Tanner stage. Receiver-operator characteristic (ROC) curves were established to assess these analytes association with a disease.

The biomarkers of the invention can be detected in a sample by any means. Methods for detecting the biomarkers are described in detail in the materials and methods and Examples which follow. For example, immunoassays, include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, fluorescent immunoassays and the like. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RITA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding an antibody of interest to the cell lysate, incubating for a period of time (e.g., 1-4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}P$ or $^{125}I$) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen (i.e. diabetic biomarker), coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well, in this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

Identification of New Markers

In a preferred embodiment, a biological sample is obtained from a patient suffering from or susceptible to diabetes. Biological samples comprising biomarkers from other patients and control subjects (i.e. normal healthy individuals of similar age, sex, physical condition) are used as comparisons. Biological samples are extracted as discussed above. Preferably, the sample is prepared prior to detection of biomarkers. Typically, preparation involves fractionation of the sample and collection of fractions determined to contain the biomarkers. Methods of pre-fractionation include, for example, size exclusion chromatography, ion exchange chromatography, heparin chromatography, affinity chromatography, sequential extraction, gel electrophoresis and liquid chromatography. The analytes also may be modified prior to detection. These methods are useful to simplify the sample for further analysis. For example, it can be useful to remove high abundance proteins, such as albumin, from blood before analysis.

In one embodiment, a sample can be pre-fractionated according to size of proteins in a sample using size exclusion chromatography. For a biological sample wherein the amount of sample available is small, preferably a size selection spin column is used. In general, the first fraction that is eluted from the column ("fraction 1") has the highest percentage of high molecular weight proteins; fraction 2 has a lower percentage of high molecular weight proteins; fraction 3 has even a lower percentage of high molecular weight proteins; fraction 4 has the lowest amount of large proteins; and so on. Each fraction can then be analyzed by immunoassays, gas phase ion spectrometry, and the like, for the detection of markers.

In another embodiment, a sample can be pre-fractionated by anion exchange chromatography. Anion exchange chromatography allows pre-fractionation of the proteins in a sample roughly according to their charge characteristics. For example, a Q anion-exchange resin can be used (Q HYPER D F, Biosepra), and a sample can be sequentially eluted with eluants having different pH's. Anion exchange chromatography allows separation of biomarkers in a sample that are more negatively charged from other types of biomarkers. Proteins that are eluted with an eluant having a high pH is likely to be weakly negatively charged, and a fraction that is eluted with an eluant having a low pH is likely to be strongly negatively charged. Thus, in addition to reducing complexity of a sample, anion exchange chromatography separates proteins according to their binding characteristics.

In yet another embodiment, a sample can be pre-fractionated by heparin chromatography. Heparin chromatography allows pre-fractionation of the markers in a sample also on the basis of affinity interaction with heparin and charge characteristics. Heparin, a sulfated mucopolysaccharide, will bind markers with positively charged moieties and a sample can be sequentially eluted with eluants having different pH's or salt concentrations. Markers eluted with an eluant having a low pH are more likely to be weakly positively charged. Markers eluted with an eluant having a high pH are more likely to be strongly positively charged. Thus, heparin chromatography also reduces the complexity of a sample and separates markers according to their binding characteristics.

In yet another embodiment, a sample can be pre-fractionated by isolating proteins that have a specific characteristic, e.g. are glycosylated. For example, a blood, or serum sample can be fractionated by passing the sample over a lectin chromatography column (which has a high affinity for sugars). Glycosylated proteins will bind to the lectin column and non-glycosylated proteins will pass through the flow through. Glycosylated proteins are then eluted from the lectin column with an eluant containing a sugar, e.g., N-acetyl-glucosamine and are available for further analysis.

Thus there are many ways to reduce the complexity of a sample based on the binding properties of the proteins in the sample, or the characteristics of the proteins in the sample.

In yet another embodiment, a sample can be fractionated using a sequential extraction protocol. In sequential extraction, a sample is exposed to a series of adsorbents to extract different types of biomarkers from a sample. For example, a sample is applied to a first adsorbent to extract certain proteins, and an eluant containing non-adsorbent proteins (i.e., proteins that did not bind to the first adsorbent) is collected. Then, the fraction is exposed to a second adsorbent. This further extracts various proteins from the fraction. This second fraction is then exposed to a third adsorbent, and so on.

Any suitable materials and methods can be used to perform sequential extraction of a sample. For example, a series of spin columns comprising different adsorbents can be used. In another example, a multi-well comprising different adsorbents at its bottom can be used. In another example, sequential extraction can be performed on a probe adapted for use in a gas phase ion spectrometer, wherein the probe surface comprises adsorbents for binding biomarkers. In this embodiment, the sample is applied to a first adsorbent on the probe, which is subsequently washed with an eluant. Markers that do not bind to the first adsorbent are removed with an eluant. The markers that are in the fraction can be applied to a second adsorbent on the probe, and so forth. The advantage of performing sequential extraction on a gas phase ion spectrometer probe is that markers that bind to various adsorbents at every stage of the sequential extraction protocol can be analyzed directly using a gas phase ion spectrometer.

In yet another embodiment, biomarkers in a sample can be separated by high-resolution electrophoresis, e.g., one or two-dimensional gel electrophoresis. A fraction containing a marker can be isolated and further analyzed by gas phase ion spectrometry. Preferably, two-dimensional gel electrophoresis is used to generate two-dimensional array of spots of biomarkers, including one or more markers. See, e.g., Jungblut and Thiede, *Mass Spectr. Rev.* 16:145-162 (1997).

The two-dimensional gel electrophoresis can be performed using methods known in the art. See, e.g., Deutscher ed., Methods In Enzymology vol. 182. Typically, biomarkers in a sample are separated by, e.g., isoelectric focusing, during which biomarkers in a sample are separated in a pH gradient until they reach a spot where their net charge is zero (i.e., isoelectric point). This first separation step results in one-dimensional array of biomarkers. The biomarkers in one dimensional array is further separated using a technique generally distinct from that used in the first separation step. For example, in the second dimension, biomarkers separated by isoelectric focusing are further separated using a polyacrylamide gel, such as polyacrylamide gel electrophoresis in the presence of sodium dodecyl sulfate (SDS-PAGE). SDS-PAGE gel allows further separation based on molecular mass of biomarkers. Typically, two-dimensional gel electrophoresis can separate chemically different biomarkers in the molecular mass range from 1000-200,000 Da within complex mixtures.

Biomarkers in the two-dimensional array can be detected using any suitable methods known in the art. For example, biomarkers in a gel can be labeled or stained (e.g., Coomassie Blue or silver staining). If gel electrophoresis generates spots that correspond to the molecular weight of one or more markers of the invention, the spot can be further analyzed by densitometric analysis or gas phase ion spectrometry. For example, spots can be excised from the gel and analyzed by gas phase ion spectrometry. Alternatively, the gel containing biomarkers can be transferred to an inert membrane by applying an electric field. Then a spot on the membrane that approximately corresponds to the molecular weight of a marker can be analyzed by gas phase ion spectrometry. In gas phase ion spectrometry, the spots can be analyzed using any suitable techniques, such as MALDI or SELDI.

Prior to gas phase ion spectrometry analysis, it may be desirable to cleave biomarkers in the spot into smaller fragments using cleaving reagents, such as proteases (e.g., trypsin). The digestion of biomarkers into small fragments provides a mass fingerprint of the biomarkers in the spot, which can be used to determine the identity of markers if desired.

In yet another embodiment, high performance liquid chromatography (HPLC) can be used to separate a mixture of biomarkers in a sample based on their different physical properties, such as polarity, charge and size. HPLC instruments typically consist of a reservoir of mobile phase, a pump, an injector, a separation column, and a detector. Biomarkers in a sample are separated by injecting an aliquot of the sample onto the column. Different biomarkers in the mixture pass through the column at different rates due to differences in their partitioning behavior between the mobile liquid phase and the stationary phase. A fraction that corresponds to the molecular weight and/or physical properties of one or more markers can be collected. The fraction can then be analyzed by gas phase ion spectrometry to detect markers.

Optionally, a marker can be modified before analysis to improve its resolution or to determine its identity. For example, the markers may be subject to proteolytic digestion before analysis. Any protease can be used. Proteases, such as trypsin, that are likely to cleave the markers into a discrete number of fragments are particularly useful. The fragments that result from digestion function as a fingerprint for the markers, thereby enabling their detection indirectly. This is particularly useful where there are markers with similar molecular masses that might be confused for the marker in question. Also, proteolytic fragmentation is useful for high molecular weight markers because smaller markers are more easily resolved by mass spectrometry. In another example, biomarkers can be modified to improve detection resolution. For instance, neuraminidase can be used to remove terminal sialic acid residues from glycoproteins to improve binding to an anionic adsorbent and to improve detection resolution. In another example, the markers can be modified by the attachment of a tag of particular molecular weight that specifically bind to molecular markers, further distinguishing them. Optionally, after detecting such modified markers, the identity of the markers can be further determined by matching the physical and chemical characteristics of the modified markers in a protein database (e.g., SwissProt).

After preparation, biomarkers in a sample are typically captured on a substrate for detection. Traditional substrates include antibody-coated 96-well plates or nitrocellulose membranes that are subsequently probed for the presence of proteins. Preferably, the biomarkers are identified using immunoassays as described above. However, preferred methods also include the use of biochips. Preferably the biochips are protein biochips for capture and detection of proteins. Many protein biochips are described in the art. These include, for example, protein biochips produced by Packard BioScience Company (Meriden Conn.), Zyomyx (Hayward, Calif.) and Phylos (Lexington, Mass.). In general, protein biochips comprise a substrate having a surface. A capture reagent or adsorbent is attached to the surface of the substrate. Frequently, the surface comprises a plurality of addressable locations, each of which location has the capture reagent bound there. The capture reagent can be a biological molecule, such as a polypeptide or a nucleic acid, which captures other biomarkers in a specific manner. Alternatively, the capture reagent can be a chromatographic material, such as an anion exchange material or a hydrophilic material. Examples of such protein biochips are described in the following patents or patent applications: U.S. Pat. No. 6,225,047 (Hutchens and Yip, "Use of retentate chromatography to generate difference maps," May 1, 2001), International publication WO 99/51773 (Kuimelis and Wagner, "Addressable protein arrays," Oct. 14, 1999), International publication WO 00/04389 (Wagner et al., "Arrays of protein-capture agents and methods of use thereof," Jul. 27, 2000), International publication WO 00/56934 (Englert et al., "Continuous porous matrix arrays," Sep. 28, 2000).

In general, a sample containing the biomarkers is placed on the active surface of a biochip for a sufficient time to allow binding. Then, unbound molecules are washed from the surface using a suitable eluant. In general, the more stringent the eluant, the more tightly the proteins must be bound to be retained after the wash. The retained protein biomarkers now can be detected by appropriate means.

Analytes captured on the surface of a protein biochip can be detected by any method known in the art. This includes, for example, mass spectrometry, fluorescence, surface plasmon resonance, ellipsometry and atomic force microscopy. Mass spectrometry, and particularly SELDI mass spectrometry, is a particularly useful method for detection of the biomarkers of this invention.

Preferably, a laser desorption time-of-flight mass spectrometer is used in embodiments of the invention. In laser desorption mass spectrometry, a substrate or a probe comprising markers is introduced into an inlet system. The markers are desorbed and ionized into the gas phase by laser from the ionization source. The ions generated are collected by an ion optic assembly, and then in a time-of-flight mass analyzer, ions are accelerated through a short high voltage field and let drift into a high vacuum chamber. At the far end of the high vacuum chamber, the accelerated ions strike a sensitive detector surface at a different time. Since the time-of-flight is a function of the mass of the ions, the elapsed time between ion formation and ion detector impact can be used to identify the presence or absence of markers of specific mass to charge ratio.

Matrix-assisted laser desorption/ionization mass spectrometry, or MALDI-MS, is a method of mass spectrometry that involves the use of an energy absorbing molecule, frequently called a matrix, for desorbing proteins intact from a probe surface. MALDI is described, for example, in U.S. Pat. No. 5,118,937 (Hillenkamp et al.) and U.S. Pat. No. 5,045,694 (Beavis and Chait). In MALDI-MS the sample is typically mixed with a matrix material and placed on the surface of an inert probe. Exemplary energy absorbing molecules include cinnamic acid derivatives, sinapinic acid ("SPA"), cyano hydroxy cinnamic acid ("CHCA") and dihydroxybenzoic acid. Other suitable energy absorbing molecules are known to those skilled in this art. The matrix dries, forming crystals that encapsulate the analyte molecules. Then the analyte molecules are detected by laser desorption/ionization mass spectrometry. MALDI-MS is useful for detecting the biomarkers of this invention if the complexity of a sample has been substantially reduced using the preparation methods described above.

Surface-enhanced laser desorption/ionization mass spectrometry, or SELDI-MS represents an improvement over MALDI for the fractionation and detection of biomolecules, such as proteins, in complex mixtures. SELDI is a method of mass spectrometry in which biomolecules, such as proteins, are captured on the surface of a protein biochip using capture reagents that are bound there. Typically, non-bound molecules are washed from the probe surface before interrogation. SELDI is described, for example, in: U.S. Pat. No. 5,719,060 ("Method and Apparatus for Desorption and Ionization of Analytes," Hutchens and Yip, Feb. 17, 1998) U.S. Pat. No. 6,225,047 ("Use of Retentate Chromatography to Generate Difference Maps," Hutchens and Yip, May 1, 2001) and Weinberger et al., "Time-of-flight mass spectrometry," in Encyclopedia of Analytical Chemistry, R. A. Meyers, ed., pp 11915-11918 John Wiley & Sons Chichesher, 2000.

Markers on the substrate surface can be desorbed and ionized using gas phase ion spectrometry. Any suitable gas phase ion spectrometers can be used as long as it allows markers on the substrate to be resolved. Preferably, gas phase ion spectrometers allow quantitation of markers.

In one embodiment, a gas phase ion spectrometer is a mass spectrometer. In a typical mass spectrometer, a substrate or a probe comprising markers on its surface is introduced into an inlet system of the mass spectrometer. The markers are then desorbed by a desorption source such as a laser, fast atom bombardment, high energy plasma, electrospray ionization, thermospray ionization, liquid secondary ion MS, field desorption, etc. The generated desorbed, volatilized species consist of preformed ions or neutrals which are ionized as a direct consequence of the desorption event. Generated ions are collected by an ion optic assembly, and then a mass analyzer disperses and analyzes the passing ions. The ions exiting the mass analyzer are detected by a detector. The detector then translates information of the detected ions into mass-to-charge ratios. Detection of the presence of markers or other substances will typically involve detection of signal intensity. This, in turn, can reflect the quantity and character of markers bound to the substrate. Any of the components of a mass spectrometer (e.g., a desorption source, a mass analyzer, a detector, etc.) can be combined with other suitable components described herein or others known in the art in embodiments of the invention.

In another embodiment, an immunoassay can be used to detect and analyze markers in a sample. This method comprises: (a) providing an antibody that specifically binds to a marker; (b) contacting a sample with the antibody; and (c) detecting the presence of a complex of the antibody bound to the marker in the sample.

To prepare an antibody that specifically binds to a marker, purified markers or their nucleic acid sequences can be used. Nucleic acid and amino acid sequences for markers can be obtained by further characterization of these markers. For example, each marker can be peptide mapped with a number of enzymes (e.g., trypsin, V8 protease, etc.). The molecular weights of digestion fragments from each marker can be used to search the databases, such as SwissProt database, for sequences that will match the molecular weights of digestion fragments generated by various enzymes. Using this method, the nucleic acid and amino acid sequences of other markers can be identified if these markers are known proteins in the databases.

Alternatively, the proteins can be sequenced using protein ladder sequencing. Protein ladders can be generated by, for example, fragmenting the molecules and subjecting fragments to enzymatic digestion or other methods that sequentially remove a single amino acid from the end of the fragment. Methods of preparing protein ladders are described, for example, in International Publication WO 93/24834 (Chait et al.) and U.S. Pat. No. 5,792,664 (Chait et al.). The ladder is then analyzed by mass spectrometry. The difference in the masses of the ladder fragments identify the amino acid removed from the end of the molecule.

If the markers are not known proteins in the databases, nucleic acid and amino acid sequences can be determined with knowledge of even a portion of the amino acid sequence of the marker. For example, degenerate probes can be made based on the N-terminal amino acid sequence of the marker. These probes can then be used to screen a genomic or cDNA library created from a sample from which a marker was initially detected. The positive clones can be identified, amplified, and their recombinant DNA sequences can be subcloned using techniques which are well known. See, e.g., Current Protocols for Molecular Biology (Ausubel et al., Green Publishing Assoc. and Wiley-Interscience 1989) and Molecular Cloning: A Laboratory Manual, 3rd Ed. (Sambrook et al., Cold Spring Harbor Laboratory, NY 2001).

Using the purified markers or their nucleic acid sequences, antibodies that specifically bind to a marker can be prepared using any suitable methods known in the art. See, e.g., Coligan, Current Protocols in Immunology (1991); Harlow & Lane, Antibodies: A Laboratory Manual (1988); Coding, Monoclonal Antibodies: Principles and Practice (2d ed. 1986); and Kohler & Milstein, *Nature* 256:495-497 (1975). Such techniques include, but are not limited to, antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275-1281 (1989); Ward et al., *Nature* 341:544-546 (1989)).

After the antibody is provided, a marker can be detected and/or quantified using any of suitable immunological binding assays known in the art (see, e.g., U.S. Pat. Nos. 4,366,241; 4,376,110; 4,517,288; and 4,837,168). Useful assays include, for example, an enzyme immune assay (EIA) such as enzyme-linked immunosorbent assay (ELISA), a radioimmune assay (RIA), a Western blot assay, or a slot blot assay. These methods are also described in, e.g., Methods in Cell Biology: Antibodies in Cell Biology, volume 37 (Asai, ed. 1993); Basic and Clinical Immunology (Stites & Terr, eds., 7th ed. 1991); and Harlow & Lane, supra.

Generally, a sample obtained from a subject can be contacted with the antibody that specifically binds the marker. Optionally, the antibody can be fixed to a solid support to facilitate washing and subsequent isolation of the complex, prior to contacting the antibody with a sample. Examples of solid supports include glass or plastic in the form of, e.g., a microtiter plate, a stick, a bead, or a microbead. Antibodies can also be attached to a probe substrate or PROTEINCHIP® array described above. The sample is preferably a biological fluid sample taken from a subject. Examples of biological fluid samples include cerebrospinal fluid, blood, serum, plasma, urine, tears, saliva etc. In a preferred embodiment, the biological fluid comprises serum. The sample can be diluted with a suitable eluant before contacting the sample to the antibody.

After incubating the sample with antibodies, the mixture is washed and the antibody-marker complex formed can be detected. This can be accomplished by incubating the washed mixture with a detection reagent. This detection reagent may be, e.g., a second antibody which is labeled with a detectable label. Exemplary detectable labels include magnetic beads (e.g., DYNABEADS™), fluorescent dyes, radiolabels, enzymes (e.g., horse radish peroxide, alkaline phosphatase and others commonly used in an ELISA), and colorimetric labels such as colloidal gold or colored glass or plastic beads. Alternatively, the marker in the sample can be detected using an indirect assay, wherein, for example, a second, labeled antibody is used to detect bound marker-specific antibody, and/or in a competition or inhibition assay wherein, for example, a monoclonal antibody which binds to a distinct epitope of the marker is incubated simultaneously with the mixture.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, marker, volume of solution, concentrations and the like. Usually the assays will be carried out at ambient temperature, although they can be conducted over a range of temperatures, such as 10° C. to 40° C.

Immunoassays can be used to determine presence or absence of a marker in a sample as well as the quantity of a marker in a sample. First, a test amount of a marker in a sample can be detected using the immunoassay methods described above. If a marker is present in the sample, it will form an antibody-marker complex with an antibody that specifically binds the marker under suitable incubation conditions described above. The amount of an antibody-marker complex can be determined by comparing to a standard. A standard can be, e.g., a known compound or another protein known to be present in a sample. As noted above, the test amount of marker need not be measured in absolute units, as long as the unit of measurement can be compared to a control.

The methods for detecting these markers in a sample have many applications. For example, one or more markers can be measured to aid in the diagnosis of diabetes and/or diabetic disorders. In another example, the methods for detection of the markers can be used to monitor responses in a subject to treatment. In another example, the methods for detecting markers can be used to assay for and to identify compounds that modulate expression of these markers in vivo or in vitro.

Data generated by desorption and detection of markers can be analyzed using any suitable means. In one embodiment, data is analyzed with the use of a programmable digital computer. The computer program generally contains a readable medium that stores codes. Certain code can be devoted to memory that includes the location of each feature on a probe, the identity of the adsorbent at that feature and the elution conditions used to wash the adsorbent. The computer also contains code that receives as input, data on the strength of the signal at various molecular masses received from a particular addressable location on the probe. This data can indicate the number of markers detected, including the strength of the signal generated by each marker.

Data analysis can include the steps of determining signal strength (e.g., height of peaks) of a marker detected and removing "outliers" (data deviating from a predetermined statistical distribution). The observed peaks can be normalized, a process whereby the height of each peak relative to some reference is calculated. For example, a reference can be background noise generated by instrument and chemicals (e.g., energy absorbing molecule) which is set as zero in the scale. Then the signal strength detected for each marker or other biomolecules can be displayed in the form of relative intensities in the scale desired (e.g., 100). Alternatively, a standard (e.g., a serum protein) may be admitted with the sample so that a peak from the standard can be used as a reference to calculate relative intensities of the signals observed for each marker or other markers detected.

The computer can transform the resulting data into various formats for displaying. In one format, referred to as "spectrum view or retentate map," a standard spectral view can be displayed, wherein the view depicts the quantity of marker reaching the detector at each particular molecular weight. In another format, referred to as "peak map," only the peak height and mass information are retained from the spectrum view, yielding a cleaner image and enabling markers with nearly identical molecular weights to be more easily seen. In yet another format, referred to as "gel view," each mass from the peak view can be converted into a grayscale image based on the height of each peak, resulting in an appearance similar to bands on electrophoretic gels. In yet another format, referred to as "3-D overlays," several spectra can be overlaid to study subtle changes in relative peak heights. In yet another format, referred to as "difference map view," two or more spectra can be compared, conveniently highlighting unique markers and markers which are up- or down-regulated between samples. Marker profiles (spectra) from any two samples may be compared visually. In yet another format, Spotfire Scatter Plot can be used, wherein markers that are detected are plotted as a dot in a plot, wherein one axis of the plot represents the apparent molecular mass of the markers detected and another axis represents the signal intensity of markers detected. For each sample, markers that are detected and the amount of markers present in the sample can be saved in a computer readable medium. This data can then be compared to a control (e.g., a profile or quantity of markers detected in control, e.g., normal, healthy subjects in whom diabetes injury is undetectable).

Diagnosis and Differentiation Between Type 1 and Type 2 Diabetes

In another aspect, the invention provides methods for aiding a type 1 diabetes, type 2 diabetes and/or diabetic disorder diagnosis using one or more markers. For example, proteins identified from patients in Table 1, peptides, fragments or derivatives thereof. These markers can be used singularly or in combination with other markers in any set. The markers are differentially present in samples of a human patient, for example a type 1 patient, and a normal subject in whom diabetes is undetectable. For example, some of the markers are expressed at an elevated level and/or are present at a higher frequency in human patients with type 1 diabetes, type 2 diabetes and/or diabetic disorders than in normal subjects. Therefore, detection of one or more of these markers in a person would provide useful information regarding the probability that the person may have type 1 versus type 2 diabetes and/or diabetic disorder. Examples of diabetic biomarkers include, but not limited to adiponectin, leptin, ghrelin, resistin, autoantibodies to insulin, autoantibodies to glutamic acid decarboxylase, autoantibodies to IL-2, autoantibodies to IA-2, incretins, TNF-α, and IL-6, fragments, variants or any combination thereof.

In a preferred embodiment, a multivariant analysis is performed associating serum adiponectin and leptin levels with anthropometrical parameters and disease state. See for example, Table 1. Specifically type 1 diabetes was diagnosed through a clinical evaluation of a number of factors including a symptomatic history (e.g., polydipsia, polyphagia, polyuria), weight loss, BMI, ketoacidosis, and the presence of a type 1 diabetes-associated autoantibody (described below). For cases of pediatric type 2 diabetes, a diagnosis was established by historical (e.g., family history of type 2 diabetes), symptomatic history, physical (e.g., BMI, race, acanthosis nigricans), and laboratory data including the absence of type 1 diabetes-associated autoantibodies (Kaufman F. Rev Endocr. Metab. Disord. 4:33-42, 2003). All healthy control subjects were also autoantibody negative.

Figure 5:
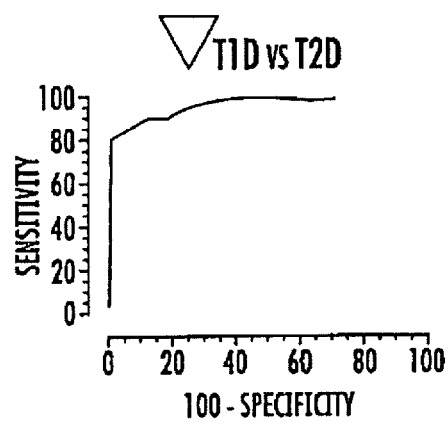
FIG. 5 is a graph showing the ROC curve for specificity and sensitivity of adiponectin-to-leptin ratio in those with type 1 diabetes (T1D) versus type 2 diabetes (T2D).

In a preferred embodiment, statistical analyses were undertaken with GraphPad Prizm 4.0 (GraphPad, San Diego, Calif.) using Fisher's exact test, receiver-operator characteristic (ROC) analysis, linear regression, t testing, or ANOVA (Kruskal-Wallis) with Dunn's post-testing. $P<0.05$ was deemed significant. ROC plots were constructed comparing type 1 with type 2 diabetic subjects (i.e., area under the ROC curve of 0.969 [95% CI 0.93-1.00]; $P<0.0001$) to determine an appropriate cutoff value for the adiponectin-to-leptin ratio (FIG. 5). At a ratio cutoff of <0.9, the sensitivity was 100% (range 80-100%) with specificity of 80% (65-91%) for type 2 as opposed to type 1 diabetes. At a ratio cutoff of <0.7, sensitivity was 88% (64-99%) with specificity of 90% (77-97%).

Accordingly, embodiments of the invention include methods for aiding a type 1 diabetes, type 2 diabetes and/or diabetic disorder diagnosis using one or more markers, wherein the method comprises: (a) detecting at least one marker in a sample, wherein the marker is adiponectin, leptin peptides, fragments and derivatives thereof; and (b) correlating the detection of the marker or markers with a probable diagnosis of type 1 diabetes, type 2 diabetes and/or diabetic disorder. The correlation may take into account the amount of the marker or markers in the sample compared to a control amount of the marker or markers (up or down regulation of the marker or markers) (e.g., in normal subjects in whom diabetes is undetectable). The correlation may take into account the presence or absence of the markers in a test sample and the frequency of detection of the same markers in a control. The correlation may take into account both of such factors to facilitate determination of whether a subject has type 1 diabetes, type 2 diabetes and/or diabetic disorder and the degree of severity of the disease, or not.

Any suitable samples can be obtained from a subject to detect markers. Preferably, a sample is a serum sample from the subject. If desired, the sample can be prepared as described above to enhance detectability of the markers. For example, to increase the detectability of markers, a blood serum sample from the subject can be preferably fractionated by, e.g., Cibacron blue agarose chromatography and single stranded DNA affinity chromatography, anion exchange chromatography and the like. Sample preparations, such as pre-fractionation protocols, is optional and may not be necessary to enhance detectability of markers depending on the methods of detection used. For example, sample preparation may be unnecessary if antibodies that specifically bind markers are used to detect the presence of markers in a sample.

Any suitable method can be used to detect a marker or markers in a sample. For example, an immunoassay or gas phase ion spectrometry can be used as described above. Using these methods, one or more markers can be detected. Preferably, a sample is tested for the presence of a plurality of markers. Detecting the presence of a plurality of markers, rather than a single marker alone, would provide more information for the diagnostician. Specifically, the detection of a plurality of markers in a sample would increase the percentage of true positive and true negative diagnoses and would decrease the percentage of false positive or false negative diagnoses.

The detection of the marker or markers is then correlated with a probable diagnosis of type 1 diabetes, type 2 diabetes and/or diabetic disorder. In some embodiments, the detection of the mere presence or absence of a marker, without quantifying the amount of marker, is useful and can be correlated with a probable diagnosis of type 1 diabetes, type 2 diabetes and/or diabetic disorder. For example, adiponectin, leptin, proteins, fragments or derivatives thereof, can be more frequently detected in patients with type 1 diabetes, type 2 diabetes and/or diabetic disorder than in normal subjects.

In other embodiments, the detection of markers can involve quantifying the markers to correlate the detection markers with a probable diagnosis of type 1 diabetes, type 2 diabetes and/or diabetic disorder, degree of severity of type 1 diabetes, type 2 diabetes and/or diabetic disorder and the like. Thus, if the amount of the markers detected in a subject being tested is higher compared to a control amount, then the subject being tested has a higher probability of having type 1 diabetes, type 2 diabetes and/or diabetic disorder.

Similarly, in another embodiment, the detection of markers can further involve quantifying the markers to correlate the detection of markers with a probable diagnosis of type 1 diabetes, type 2 diabetes and/or diabetic disorder, degree of severity of type 1 diabetes, type 2 diabetes and/or diabetic disorder and the like, wherein the markers are present in lower quantities in blood serum samples from patients than in blood serum samples of normal subjects. Thus, if the amount of the markers detected in a subject being tested is lower compared to a control amount, then the subject being tested has a higher probability of having type 1 diabetes, type 2 diabetes and/or diabetic disorder.

When the markers are quantified, it can be compared to a control. A control can be, e.g., the average or median amount of marker present in comparable samples of normal subjects in whom type 1 diabetes, type 2 diabetes and/or diabetic disorder, is undetectable. The control amount is measured under the same or substantially similar experimental conditions as in measuring the test amount. For example, if a test sample is obtained from a subject's blood serum sample and a marker is detected using a particular probe, then a control amount of the marker is preferably determined from a serum sample of a patient using the same probe. It is preferred that the control amount of marker is determined based upon a significant number of samples from normal subjects who do not have type 1 diabetes, type 2 diabetes and/or diabetic disorder so that it reflects variations of the marker amounts in that population.

Data generated by mass spectrometry can then be analyzed by a computer software. The software can comprise code that converts signal from the mass spectrometer into computer readable form. The software also can include code that applies an algorithm to the analysis of the signal to determine whether the signal represents a "peak" in the signal corresponding to a marker of this invention, or other useful markers. The software also can include code that executes an algorithm that compares signal from a test sample to a typical signal characteristic of "normal" and human type 1 diabetes, type 2 diabetes and/or diabetic disorder and determines the closeness of fit between the two signals. The software also can include code indicating which the test sample is closest to, thereby providing a probable diagnosis.

Production of Antibodies to Detect Type 1 Diabetes and Type 2 Diabetes Biomarkers Biomarkers obtained from samples in patients suffering from type 1 diabetes, type 2 diabetes and/or diabetic disorder, degrees of severity of type 1 diabetes, type 2 diabetes and/or diabetic disorder and the like, can be prepared as described above. Furthermore, diabetic biomarkers can be subjected to enzymatic digestion to obtain fragments or peptides of the biomarkers for the production of antibodies to different antigenic epitopes that can be present in a peptide versus the whole protein. Antigenic epitopes are useful, for example, to raise antibodies, including monoclonal antibodies, that specifically bind the epitope. Antigenic epitopes can be used as the target molecules in immunoassays. (See, for instance, Wilson et al., *Cell* 37:767-778 (1984); Sutcliffe et al., *Science* 219:660-666 (1983)).

Diabetic biomarker epitopes can be used, for example, to induce antibodies according to methods well known in the art. (See, for instance, Sutcliffe et al., supra; Wilson et al., supra; Chow et al., *Proc. Natl. Acad. Sci.* USA 82:910-914; and Bittle et al., *J. Gen. Virol.* 66:2347-2354 (1985). Diabetic polypeptides comprising one or more immunogenic epitopes may be presented for eliciting an antibody response together with a carrier protein, such as an albumin, to an animal system (such as rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., *J. Gen. Virol.*, 66:2347-2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 µg of peptide or carrier protein and Freund's adjuvant or any other adjuvant known for stimulating an immune response. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

Nucleic acids diabetic biomarker epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, *Proc. Natl. Acad. Sci. USA* 88:8972-897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with the recombinant vaccinia virus are loaded onto $Ni^{2+}$ nitriloacetic acid-agarose column and histidine-tagged proteins can be selectively eluted with imidazole-containing buffers.

The antibodies of the present invention may be generated by any suitable method known in the art. The antibodies of the present invention can comprise polyclonal antibodies. Methods of preparing polyclonal antibodies are known to the skilled artisan (Harlow, et al., Antibodies: A Laboratory Manual, (Cold spring Harbor Laboratory Press, 2nd ed. (1988), which is hereby incorporated herein by reference in its entirety). For example, a polypeptide of the invention can be administered to various host animals including, but not limited to, rabbits, mice, rats, etc. to induce the production of sera containing polyclonal antibodies specific for the antigen. The administration of the polypeptides of the present invention may entail one or more injections of an immunizing agent and, if desired, an adjuvant. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art. For the purposes of the invention, "immunizing agent" may be defined as a polypeptide of the invention, including fragments, variants, and/or derivatives thereof, in addition to fusions with heterologous polypeptides and other forms of the polypeptides as may be described herein.

Typically, the immunizing agent and/or adjuvant will be injected in the mammal by multiple subcutaneous or intraperitoneal injections, though they may also be given intramuscularly, and/or through IV. The immunizing agent may include polypeptides of the present invention or a fusion protein or variants thereof. Depending upon the nature of the polypeptides (i.e., percent hydrophobicity, percent hydrophilicity, stability, net charge, isoelectric point etc.), it may be useful to conjugate the immunizing agent to a protein known to be immunogenic in the mammal being immunized. Such conjugation includes either chemical conjugation by derivatizing active chemical functional groups to both the polypeptide of the present invention and the immunogenic protein such that a covalent bond is formed, or through fusion-protein based methodology, or other methods known to the skilled artisan. Examples of such immunogenic proteins include, but are not limited to keyhole limpet hemocyanin, serum albumin, bovine thyroglobulin, and soybean trypsin inhibitor. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Additional examples of adjuvants which may be employed includes the MPL-TDM adjuvant (monophosphoryl lipid A, synthetic trehalose dicorynomycolate). The immunization protocol may be selected by one skilled in the art without undue experimentation.

The antibodies of the present invention can also comprise monoclonal antibodies. Monoclonal antibodies may be prepared using hybridoma methods, such as those described by Kohler and Milstein, *Nature,* 256:495 (1975) and U.S. Pat. No. 4,376,110, by Harlow, et al., Antibodies: A Laboratory Manual, (Cold spring Harbor Laboratory Press, 2nd ed, (1988), by Hammerling, et al., Monoclonal Antibodies and T-Cell Hybridomas (Elsevier, N.Y., (1981)), or other methods known to the artisan. Other examples of methods which may be employed for producing monoclonal antibodies includes, but are not limited to, the human B-cell hybridoma technique (Kosbor et al., 1983, *Immunology Today* 4:72; Cole et al., 1983, *Proc. Natl. Acad. Sci.* USA 80:2026-2030), and the EBV-hybridoma technique (Cole et al., 1985, Monoclonal Antibodies And Cancer Therapy, Alan R. Liss, Inc., pp. 77-96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In a hybridoma method, a mouse, a humanized mouse, a mouse with a human immune system, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include polypeptides identified in diabetes patients, fragments or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, (1986), pp. 59-103). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. As inferred throughout the specification, human myeloma and mouse-human heteromyeloma cell lines also have been described for the production of human monoclonal antibodies (Kozbor, *J. Immunol.,* 133:3001 (1984); Brodeur et al., Monoclonal Antibody Production Techniques and Applications, Marcel Dekker, Inc., New York, (1987) pp. 51-63).

The culture medium in which the hybridoma cells are cultured can then be assayed for the presence of monoclonal antibodies directed against the adiponectin and/or lectin polypeptides of the present invention. Preferably, the binding specificity of monoclonal antibodies produced by the hybridoma cells is determined by immunoprecipitation or by an in vitro binding assay, such as radioimmunoassay (RIA) or enzyme-linked immunoadsorbant assay (ELISA). Such techniques are known in the art and within the skill of the artisan. The binding affinity of the monoclonal antibody can, for example, be determined by the Scatchard analysis of Munson and Pollart, *Anal. Biochem.*, 107:220 (1980).

After the desired hybridoma cells are identified, the clones may be subcloned by limiting dilution procedures and grown by standard methods (Goding, supra). Suitable culture media for this purpose include, for example, Dulbecco's Modified Eagle's Medium and RPMI-1640. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-sepharose, hydroxyapatite chromatography, gel exclusion chromatography, gel electrophoresis, dialysis, or affinity chromatography.

The skilled artisan would acknowledge that a variety of methods exist in the art for the production of monoclonal antibodies and thus, the invention is not limited to their sole production in hybridomas. For example, the monoclonal antibodies may be made by recombinant DNA methods, such as those described in U.S. Pat. No. 4,816,567. In this context, the term "monoclonal antibody" refers to an antibody derived from a single eukaryotic, phage, or prokaryotic clone. The DNA encoding the monoclonal antibodies of the invention can be readily isolated and sequenced using conventional procedures (e.g., by using oligonucleotide probes that are capable of binding specifically to genes encoding the heavy and light chains of murine antibodies, or such chains from human, humanized, or other sources). The hybridoma cells of the invention serve as a preferred source of such DNA. Once isolated, the DNA may be placed into expression vectors, which are then transformed into host cells such as Simian COS cells, Chinese hamster ovary (CHO) cells, or myeloma cells that do not otherwise produce immunoglobulin protein, to obtain the synthesis of monoclonal antibodies in the recombinant host cells.

Methods for producing and screening for specific antibodies using hybridoma technology are routine and well known in the art. In a non-limiting example, mice can be immunized with a biomarker polypeptide or a cell expressing such peptide. Once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention. The antibodies detecting diabetic biomarkers, peptides and derivatives thereof, can be used in immunoassays and other methods to identify new diabetic biomarkers and for use in the diagnosis of type 1 diabetes, type 2 diabetes and/or diabetic disorder.

Other methods can also be used for the large scale production of diabetic biomarker specific antibodies. For example, antibodies can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., *J. Immunol. Methods* 182:41-50 (1995); Ames et al., *Immunol. Methods* 184:177-186 (1995); Kettleborough et al., *Eur. J. Immunol.* 24:952-958 (1994); Persic et al., Gene 187 9-18 (1997); Burton et al., Advances in Immunology 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated in pertinent part by reference herein for the reasons cited in the above text.

The antibodies of the present invention have various utilities. For example, such antibodies may be used in diagnostic assays to detect the presence or quantification of the polypeptides of the invention in a sample. Such a diagnostic assay can comprise at least two steps. The first, subjecting a sample with the antibody, wherein the sample is a tissue (e.g., human, animal, etc.), biological fluid (e.g., blood, urine, sputum, semen, amniotic fluid, saliva, etc.), biological extract (e.g., tissue or cellular homogenate, etc.), a protein microchip (e.g., See Arenkov P, et al., *Anal Biochem.*, 278(2):123-131 (2000)), or a chromatography column, etc. And a second step involving the quantification of antibody bound to the substrate. Alternatively, the method may additionally involve a first step of attaching the antibody, either covalently, electrostatically, or reversibly, to a solid support, and a second step of subjecting the bound antibody to the sample, as defined above and elsewhere herein.

Various diagnostic assay techniques are known in the art, such as competitive binding assays, direct or indirect sandwich assays and immunoprecipitation assays conducted in either heterogeneous or homogenous phases (Zola, Monoclonal Antibodies: A Manual of Techniques, CRC Press, Inc., (1987), pp 147-158). The antibodies used in the diagnostic assays can be labeled with a detectable moiety. The detectable moiety should be capable of producing, either directly or indirectly, a detectable signal. For example, the detectable moiety may be a radioisotope, such as $^2H$, $^{14}C$, $^{32}P$, or $^{125}I$, a florescent or chemiluminescent compound, such as fluorescein isothiocyanate, rhodamine, or luciferin, or an enzyme, such as alkaline phosphatase, beta-galactosidase, green fluorescent protein, or horseradish peroxidase. Any method known in the art for conjugating the antibody to the detectable moiety may be employed, including those methods described by Hunter et al., *Nature,* 144:945 (1962); David et al., *Biochem.,* 13:1014 (1974); Pain et al., *J. Immunol. Methods,* 40:219 (1981); and Nygren, *J. Histochem. and Cytochem.,* 30:407 (1982).

Kits

In yet another aspect, the invention provides kits for aiding a diagnosis of type 1 diabetes, type 2 diabetes and/or diabetic disorder and degree of severity of type 1 diabetes, type 2 diabetes and/or diabetic disorder, wherein the kits can be used to detect the markers of the present invention. For example, the kits can be used to detect any one or more of the markers described herein, which markers are differentially present in samples of a patient and normal subjects. For example, adiponectin, leptin, ghrelin, resistin, autoantibodies to insulin, autoantibodies to glutamic acid decarboxylase, autoantibodies to IA-2, autoantibodies to IA-2, incretins, TNF-α, and IL-6, fragments, variants or any combination thereof. The kits of the invention have many applications. For example, the kits can be used to differentiate if a subject has type 1 versus type 2 diabetes, or has a negative diagnosis, thus aiding type 1 diabetes, type 2 diabetes and/or diabetic disorder diagnosis. In another example, the kits can be used to identify compounds that modulate expression of one or more of the markers in in vitro or in vivo animal models to determine the effects of treatment.

In one embodiment, a kit comprises (a) an antibody that specifically binds to a marker; and (b) a detection reagent. Such kits can be prepared from the materials described above, and the previous discussion regarding the materials (e.g., antibodies, detection reagents, immobilized supports, etc.) is fully applicable to this section and will not be repeated. Optionally, the kit may further comprise pre-fractionation spin columns. In some embodiments, the kit may further comprise instructions for suitable operation parameters in the form of a label or a separate insert.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or colorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Optionally, the kit may further comprise a standard or control information so that the test sample can be compared with the control information standard to determine if the test amount of a marker detected in a sample is a diagnostic amount consistent with a diagnosis of type 1 diabetes, type 2 diabetes and/or diabetic disorder, degree of severity of type 1 diabetes, type 2 diabetes and/or diabetic disorder, and/or effect of treatment on the patient.

In another embodiment, a kit comprises: (a) a substrate comprising an adsorbent thereon, wherein the adsorbent is suitable for binding a marker, and (b) instructions to detect the marker or markers by contacting a sample with the adsorbent and detecting the marker or markers retained by the adsorbent. In some embodiments, the kit may comprise an eluant (as an alternative or in combination with instructions) or instructions for making an eluant, wherein the combination of the adsorbent and the eluant allows detection of the markers using gas phase ion spectrometry. Such kits can be prepared from the materials described above, and the previous discussion of these materials (e.g., probe substrates, adsorbents, washing solutions, etc.) is fully applicable to this section and will not be repeated.

In another embodiment, the kit may comprise a first substrate comprising an adsorbent thereon (e.g., a particle functionalized with an adsorbent) and a second substrate onto which the first substrate can be positioned to form a probe which is removably insertable into a gas phase ion spectrometer. In other embodiments, the kit may comprise a single substrate which is in the form of a removably insertable probe with adsorbents on the substrate. In yet another embodiment, the kit may further comprise a pre-fractionation spin column (e.g., Cibacron blue agarose column, anti-HSA agarose column, size exclusion column, Q-anion exchange spin column, single stranded DNA column, lectin column, etc.).

Optionally, the kit can further comprise instructions for suitable operational parameters in the form of a label or a separate insert. For example, the kit may have standard instructions informing a consumer how to wash the probe after a sample is contacted on the probe. In another example, the kit may have instructions for pre-fractionating a sample to reduce complexity of proteins in the sample. In another example, the kit may have instructions for automating the fractionation or other processes.

The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted. By their citation of various references in this document, Applicants do not admit any particular reference is "prior art" to their invention.

EXAMPLES

Materials and Methods

Samples from children and adolescents with type 1 diabetes (n=41), type 2 diabetes (n=17), and nondiabetic individuals of similar age from the general population (n=43) were investigated. An analysis included the parameters of matching for BMI and Tanner stage. Receiver-operator characteristic (ROC) curves were established to assess these analytes association with a disease.

Adiponectin and leptin levels were measured in a single serum sample (nonfasting, stored at −80° C.) from children and adolescents with type 1 diabetes, type 2 diabetes, and nondiabetic individuals of similar age from the general population (demographics in legend to Table 1). Type 1 and type 2 diabetes were diagnosed according to American Diabetes Association criteria (Expert Committee on the Diagnosis and Classification of Diabetes Mellitus: Report of the Expert Committee on the Diagnosis and Classification of Diabetes Mellitus. *Diabetes Care* 26 (Suppl. 1):S5-S20, 2003).

Specifically type 1 diabetes was diagnosed through a clinical evaluation of a number of factors including a symptomatic history (e.g., polydipsia, polyphagia, polyuria), weight loss, BMI, ketoacidosis, and the presence of a type 1 diabetes-associated autoantibody (described below). For cases of pediatric type 2 diabetes, a diagnosis was established by historical (e.g., family history of type 2 diabetes), symptomatic history, physical (e.g., BMI, race, acanthosis nigricans), and laboratory data including the absence of type 1 diabetes-associated autoantibodies (Kaufman F. *Rev Endocr. Metab. Disord.* 4:33-42, 2003). All healthy control subjects were also autoantibody negative.

Serum Analyte and Autoantibody Detection

LINCOPLEX™ (Linco Research, St. Louis, Mo.) kits were used for the measurement of human leptin (sensitivity 0.01 ng/ml; interassay coefficient of variation [CV] 5.0%), while B-Bridge International (San Jose, Calif.) human adiponectin enzyme-linked immunosorbent assay kits were used for monitoring serum adiponectin levels (lower limit 0.02 ng/ml; interassay CV 3.2%). To reduce the potential for interfering heterophile or natural antibodies, a serum matrix diluent was provided by the manufacturer of the assay kits. Tests for autoantibodies against three type 1 diabetes-associated autoantigens performed in all study participants, including those against insulin autoantibody, GAD antibody, and insulinoma-associated protein 2 antigen. Assays were performed as previously described (She J. S., et al. *Proc Natl. Acad, Sci* USA 96:8116-8119, 1999).

Statistics

All statistical analyses were undertaken with GraphPad Prizm 4.0 (GraphPad, San Diego, Calif.) using Fisher's exact test, receiver-operator characteristic (ROC) analysis, linear regression, t testing, or ANOVA (Kruskal-Wallis) with Dunn's post-testing. P<0.05 was deemed significant.

Example 1

Determination of Adiponectin and Leptin Levels In Vivo

Adiponectin and leptin levels were determined in 18 T2D children (11M/12F; median age 14 years, range 10-20 years), 20 non-diabetic age matched individuals from the general population (11M/9F; median age 12.0 years, range 5-21 years), as well as 44 T1D patients (22M/22F; median age 14.0 years, range 6-20 years). Signed (IRB approved) informed consents and assents were obtained from the children and their parents. LINCOPLEX™ (Linco Research, St. Louis, Mo., USA) kits were used for measurement of human leptin (sensitivity, 23.4 pg/mL; assay range, 0.375 ng/mL to 12 ng/mL; intra-assay CV=4.6-5.8%; inter-assay CV=3.2-7.4%), while B-Bridge International (San Jose, Calif., USA) human adiponectin ELISA kits were used for monitoring serum adiponectin levels (sensitivity, 23.4 pg/mL; assay range, 0.375 ng/mL to 12 ng/mL; intra-assay CV=4.6-5.8%; inter-assay CV=3.2-7.4%). T1D related autoantibody assays were performed for anti-insulin (IAA), anti-glutamic acid decarboxylase (GADA), and anti-IA2 autoantibodies (IA-2A). All radiobinding assays were subjected to utilising an index cut-off for positivity based on previously investigated control populations. All statistical analyses were undertaken with GraphPad Prizm.

Figure 1B:
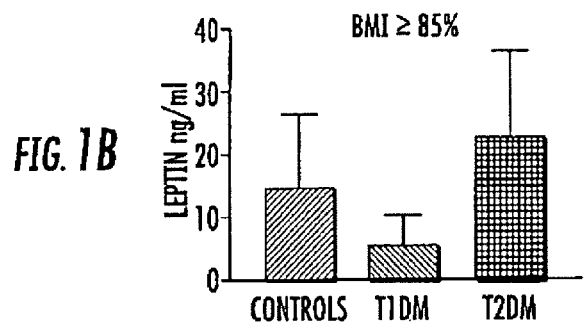

Leptin levels were directly correlated with BMI for the entire pediatric population studied (r=0.62; p<0.0001). This association was also observed when analyzed as a function of disease status. After adjustment to analysis of subjects whose BMI> or equal to $85^{th}$ percentile, children with T2D had significantly higher leptin levels than healthy children (FIG. 1B; p<0.003), while those with T1D demonstrated reduced levels in comparison to healthy children (FIG. 1B; p<0.001). Without adjustment for BMI, a similar trend was observed in that mean leptin levels were elevated in T2D subjects (23.1 ng/ml (15.6-30.6)) versus all healthy controls (7.4 ng/ml (2.8-12); p<0.0004) or T1D subjects (4.5 ng/ml (3.3-5.7); p<0.001). Leptin concentrations were gender-dependent, being higher among females (11.4 ng/ml (7.6-15.1)) than males (6.3 ng/ml (3.2-9.4); p<0.003) regardless of their diagnosis and BMI.

Figure 1C:
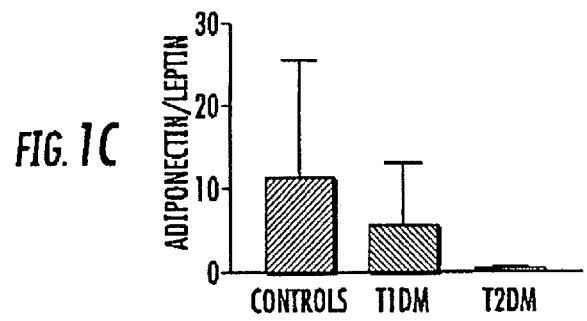
Figure 1D:
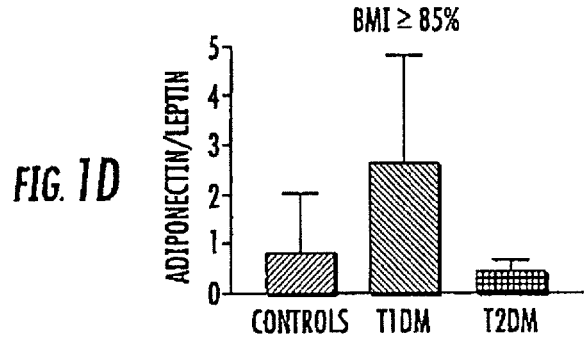

Adiponectin to leptin ratios revealed an even more striking difference between T1D and T2D children. Adiponectin/leptin ratios were dramatically different amongst healthy children (11.8 (4.8-18.7)) and those with T1D (6.1 (3.8-8.3)) or T2D (0.4 (0.3-0.5)) (FIG. 1C; p<0.0001). As anticipated, when restricting analysis to include only those with BMI> or equal to $85^{th}$ percentile (FIG. 1D) or Tanner 4-5, the ratios decrease since increases in BMI positively associate with increasing leptin or pubertal stage and decreases in Adiponectin. Despite this, the ratio for T1D was significantly elevated versus T2D subjects (p<0.0001).

Example 2

Adiponectin Levels in Children and Adolescents

Figure 2A:
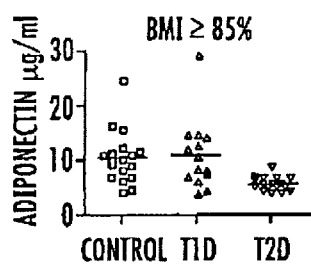
FIGS. 2A-2F are graphs showing adiponectin and leptin levels in healthy pediatric subjects and those with diabetes. Serum adiponectin levels in indicated subject groups with BMI>85 percentile (FIG. 2A), those with Tanner 4 or 5 (FIG. 2B), or all study participants (FIG. 2C). Serum leptin levels in study subject groups with BMI>85 percentile (FIG. 2D), those with Tanner 4 or 5 (FIG. 2E), or all study participants (FIG. 2F). Bar represents mean value. T1D (type 1 diabetes); T2D (type 2 diabetes).
Figure 2B:
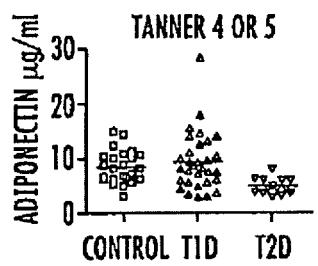
Figure 2C:
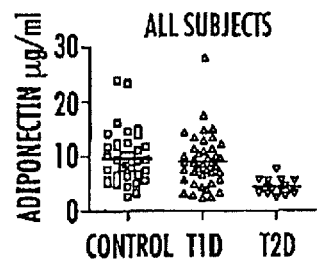

Adiponectin levels were inversely correlated with BMI for the entire pediatric population studied ($r^2$=0.60; P<0.0001). Analysis of subjects with BMI was >$85^{th}$ percentile indicated that control subjects had higher adiponectin levels than type 2 diabetic subjects (FIG. 2A; control versus type 2 diabetic subjects, P<0.01). Type 1 diabetic subjects were not significantly different from healthy control subjects (P=NS), yet type 1 diabetic subjects were higher than those with type 2 diabetes (P<0.01). There was no correlation between adiponectin levels and sex, but levels were lower in subjects with type 2 diabetes who were Tanner stage 4 or 5 (FIG. 2B; control versus type 1 diabetic subjects, P=NS; control versus type 2 diabetic subjects, P<0.01; and type 1 diabetic versus type 2 diabetic subjects, P<0.01). The adiponectin levels in the pediatric type 1 diabetic subjects (FIG. 2C; 10.2 µg/ml

[95% CI 8.6-11.7]) did not differ from healthy control subjects (10.6 μg/ml [9.2-12.0]; P=NS). Children with type 2 diabetes (5.5 μg/ml [4.8-6.2]) had significantly lower adiponectin levels than both of those groups (control versus type 2 diabetic subjects, P<0.001; type 1 diabetic versus type 2 diabetic subjects, P<0.01).

Example 3

Childhood and Adolescent Leptin Levels

Figure 2D:
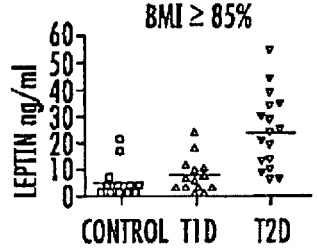
Figure 2E:
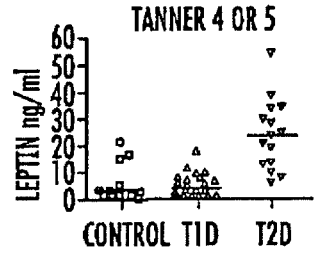
Figure 2F:
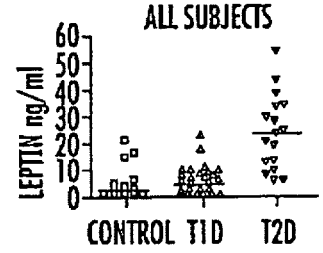

Leptin levels were directly correlated with BMI for the entire pediatric population studied ($r^2=0.60$; P<0.0001). This association was also observed when analyzed as a function of disease status. An analysis of subjects whose BMI was >$85^{th}$ percentile (FIG. 2D; control versus type 2 diabetic subjects, P<0.001; type 1 diabetic versus type 2 diabetic subjects, P<0.01) or those with Tanner stage 4 and 5 (FIG. 2E; control versus type 2 diabetic subjects, P<0.001; type 1 diabetic versus type 2 diabetic subjects, P<0.001) indicated children with type 2 diabetes had significantly higher leptin levels than healthy children and those with type 1 diabetes. However, leptin levels were not different between type 1 diabetic and control subjects if evaluating those >$85^{th}$ percentile (control versus type 1 diabetic subjects; P=NS) or with Tanner stage 4 and 5 (control versus type 1 diabetic subjects; P=NS). Leptin concentrations were somewhat higher (albeit not statistically significant) among females (7.1 ng/ml [95% CI 5.5-8.7]) than males (5.2 ng/ml [3.8-6.6]; P=0.061), regardless of their diagnosis and BMI. Without accounting for BMI (i.e., all subjects), a trend was observed in that mean leptin levels were elevated in type 2 diabetic subjects (FIG. 2F; 24.3 ng/ml [17.1-31.5]) versus all healthy control (2.7 ng/ml [1.3-4.1]; P<0.001) or type 1 diabetic (5.1 ng/ml [3.5-6.7]; P<0.001) subjects. Leptin levels were also modestly elevated in type 1 diabetic subjects compared with control subjects (P<0.05).

Example 4

Adiponectin-to-Leptin Ratios

Figure 3:
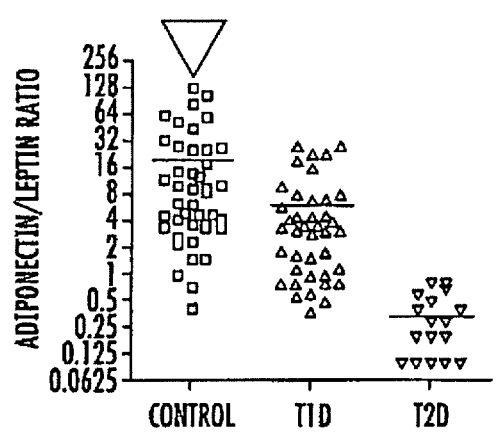
FIG. 3 is a graph showing adiponectin and leptin levels in healthy pediatric subjects and those with diabetes. Serum adiponectin to leptin ratios in indicated subject groups. Bar represents mean value; y-axis, $\log_2$ scale. T1D (type 1 diabetes); T2D (type 2 diabetes).
Figure 4:
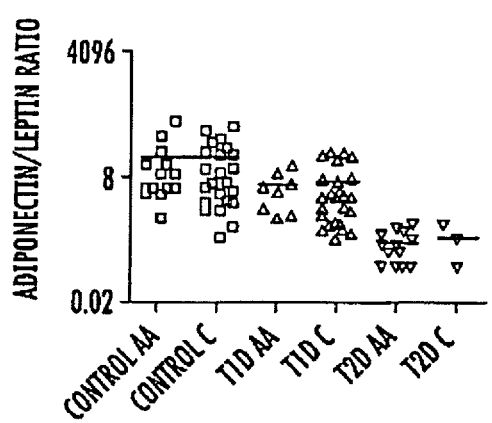
FIG. 4 is a graph showing adiponectin and leptin ratios in healthy pediatric subjects and those with diabetes as a function of race. Bar represents mean value; y-axis, $\log_2$ scale. AA (African American); C (Caucasian); T1D (type 1 diabetes); T2D (type 2 diabetes).

An exploration of adiponectin-to-leptin ratios revealed an even more striking difference between type 1 and type 2 diabetic children. Adiponectin-to-leptin ratios were dramatically different among healthy (20.2 [95% CI 11.3-29.0]) and type 1 diabetic (6.3 [3.8-8.8]) children than those with type 2 diabetes (0.3 [0.2-0.5]) (FIG. 3; control versus type 1 diabetic subjects, P=NS; control versus type 2 diabetic subjects, P<0.001; type 1 diabetic versus type 2 diabetic subjects, P<0.001). When restricting analysis to include only those subjects with BMI>$85^{th}$ percentile (control versus type 1 diabetic subjects, P~NS; control versus type 2 diabetic subjects, P<0.001; type 1 diabetic versus type 2 diabetic subjects, P<0.01) or Tanner stage 4 and 5 (control versus type 1 diabetic subjects, P<NS; control versus type 2 diabetic subjects, P<0.001; type 1 diabetic versus type 2 diabetic subjects, P<0.001), the ratios decrease because increases in BMI positively associate with increasing leptin or pubertal stage and decreases in adiponectin. Despite this, the ratio for type 1 diabetic and control subjects was significantly elevated versus type 2 diabetic subjects (P<0.001). To ascertain potential influences of ethnicity, an analysis was performed that compared adiponectin-to-leptin ratios as a function of race (FIG. 4). No differences were observed in this ratio when comparing Caucasian and African American subjects within the same disease group (all P=NS).

Example 5

Diagnostic Value

ROC plots were constructed comparing type 1 with type 2 diabetic subjects (i.e., area under the ROC curve of 0.969 [95% CI 0.93-1.00]; P<0.0001) to determine an appropriate cutoff value for the adiponectin-to-leptin ratio (FIG. 5). At a ratio cutoff of <0.9, the sensitivity was 100% (range 80-100%) with specificity of 80% (65-91%) for type 2 as opposed to type 1 diabetes. At a ratio cutoff of <0.7, sensitivity was 88% (64-99%) with specificity of 90% (77-97%).

TABLE 1

Anthropometrical and ethnic variables in the study population

| | Type 2 diabetes | Type 1 diabetes | Healthy Control subjects |
|---|---|---|---|
| n | 17 | 4 | 43 |
| Age (years) | 144 (10-20) | 13.2 (9-20) | 13.7 (6-21) |
| Men/Women | 4/13 | 21/20 | 22/21 |
| Tanner | 4.4 (2-5) | 3.9 (1-5) | 3.3 (1-5) |
| BMI (kg/m²) | 36 (32.6-39.4) | 21.7 (20.4-23.1) | 20.5 (18.8-22.3) |
| Disease duration (years) | 2.4 (0.1-7) | 3.9 (0.1-10) | NA |
| Ethnicity (%) | | | |
| Caucasian | 18 | 7 | 62 |
| African American | 75 | 2 | 33 |
| Latino | 6 | 7 | 5 |
| Treatment | Combination of oral hypoglycemic agents with/without insulin | Insulin | NA |

Data are mean (range) unless otherwise indicated.
Data for BMI are mean (95% CI).
No healthy control subject (or any type 2 diabetic subject by their differential diagnosis) was identified with any of three type 1 diabetes-associated autoantibodies. In contrast, frequencies of 50-70% positivity were observed for those autoantibodies in the type 1 diabetic group.
NA, not applicable.

All publications, patent applications, patents, and other references mentioned herein are incorporated in pertinent part by reference herein for the reasons cited in the above text.

We claim:

1. A method for differentiating between and treating type 1 and type 2 diabetes in pediatric and adolescent subjects, the method comprising the steps of:
    (a) obtaining a sample from the subject;
    (b) determining the amount of adiponectin and the amount of leptin in the sample;
    (c) calculating a ratio of the amount of adiponectin and the amount of leptin in the sample;
    (d) correlating the ratio with the presence of type 1 diabetes or type 2 diabetes;
    (e) diagnosing either type 1 or type 2 diabetes; and
    (f) based on the diagnosis of step (e), treating the patient for either type 1 or type 2 diabetes, wherein a ratio of the amount of adiponectin in micrograms/ml to the amount of leptin in nanograms/ml in the sample equaling less than approximately 0.9 is indicative of type 2 diabetes in the subject; and
    wherein the subject has a BMI greater than $85^{th}$ percentile.

2. The method of claim 1, wherein the amounts of leptin and adiponectin are determined using an immunoassay.

3. The method of claim 2, wherein the immunoassay is an ELISA.

4. The method of claim 1, wherein proteins, peptides, or derivatives thereof of leptin or adiponectin are detected.

5. The method of claim 1, wherein the sample is selected from the group consisting of blood, blood plasma, serum, urine, tissue, cells, and organs.

6. The method of claim 1, wherein leptin and adiponectin are detected using a biochip array.

7. The method of claim 6, wherein the biochip array is a protein chip array.

8. The method of claim 7, wherein the surface of the biochip array comprises one or more antibodies.

9. The method of claim 6, wherein the leptin and adiponectin are immobilized on the biochip array.

10. The method of claim 9, wherein immobilized leptin and adiponectin are subjected to laser ionization to detect the molecular weight of the leptin and adiponectin.

11. The method of claim 1, wherein in step (b) leptin and adiponectin are detected using laser desorption/ionization mass spectrometry, comprising:

providing a probe adapted for use with a mass spectrometer comprising an adsorbent attached thereto, and;

contacting the subject sample with the adsorbent, and;

desorbing and ionizing the leptin and adiponectin from the probe and detecting the deionized/ionized leptin and adiponectin with the mass spectrometer.

12. The method of claim 11, wherein laser desorption/ionization mass spectrometry comprises:

providing a substrate comprising an adsorbent attached thereto;

contacting the subject sample with the adsorbent;

placing the substrate on a probe adapted for use with a mass spectrometer comprising an adsorbent attached thereto; and, desorbing and ionizing the leptin and adiponectin from the probe and detecting the desorbed/ionized leptin and adiponectin with the mass spectrometer.

13. The method of claim 11, wherein the adsorbent is an antibody.

* * * * *

UNITED STATES PATENT AND TRADEMARK OFFICE
CERTIFICATE OF CORRECTION

PATENT NO. : 8,594,949 B2  
APPLICATION NO. : 13/245287  
DATED : November 26, 2013  
INVENTOR(S) : Tamir M. Ellis et al.

Page 1 of 1

It is certified that error appears in the above-identified patent and that said Letters Patent is hereby corrected as shown below:

In the Specification:

Column 11,

Line 21, "RITA buffer" should read --RIPA buffer--.

Column 17,

Line 37, "Coding," should read --Goding,--.

Signed and Sealed this
Twenty-fifth Day of March, 2014

Michelle K. Lee
*Deputy Director of the United States Patent and Trademark Office*